(12) United States Patent
Randu et al.

(10) Patent No.: US 10,888,088 B2
(45) Date of Patent: Jan. 12, 2021

(54) CONCENTRATE COMPRISING A MEL AND A POLYETHYLENE GLYCOL FATTY ACID ESTER HAVING AN HLB VALUE GREATER THAN OR EQUAL TO 12

(71) Applicant: OLEON NV, Evergem (BE)

(72) Inventors: Marion Randu, Clermont (FR); Sylvie Hery, Jaux (FR); Pierre Ravier, Compiegne (FR); Sophie Deprey, Margny-les-Compiegne (FR)

(73) Assignee: OLEON NV, Evergem (BE)

( * ) Notice: Subject to any disclaimer, the term of this patent is extended or adjusted under 35 U.S.C. 154(b) by 0 days.

(21) Appl. No.: 16/085,348

(22) PCT Filed: Mar. 17, 2017

(86) PCT No.: PCT/EP2017/056465
§ 371 (c)(1),
(2) Date: Sep. 14, 2018

(87) PCT Pub. No.: WO2017/158194
PCT Pub. Date: Sep. 21, 2017

(65) Prior Publication Data
US 2019/0082683 A1 Mar. 21, 2019

(30) Foreign Application Priority Data
Mar. 17, 2016 (FR) .................... 16 52288

(51) Int. Cl.
| | | |
|---|---|---|
| *A01N 25/30* | (2006.01) | |
| *A01N 25/04* | (2006.01) | |
| *A61K 8/86* | (2006.01) | |
| *A61K 8/60* | (2006.01) | |
| *A61K 8/39* | (2006.01) | |
| *A01N 43/16* | (2006.01) | |
| *A61Q 19/00* | (2006.01) | |
| *A01N 25/02* | (2006.01) | |
| *C11D 1/66* | (2006.01) | |
| *C11D 1/74* | (2006.01) | |
| *A61K 8/06* | (2006.01) | |
| *A61K 8/37* | (2006.01) | |

(52) U.S. Cl.
CPC ............ *A01N 25/30* (2013.01); *A01N 25/02* (2013.01); *A01N 25/04* (2013.01); *A01N 43/16* (2013.01); *A61K 8/06* (2013.01); *A61K 8/37* (2013.01); *A61K 8/39* (2013.01); *A61K 8/602* (2013.01); *A61K 8/604* (2013.01); *A61K 8/86* (2013.01); *A61Q 19/00* (2013.01); *C11D 1/667* (2013.01); *C11D 1/74* (2013.01); *A61K 2800/10* (2013.01)

(58) Field of Classification Search
None
See application file for complete search history.

(56) References Cited

U.S. PATENT DOCUMENTS

2005/0042245 A1* 2/2005 Taranta .................. A01N 25/04
424/405
2013/0142855 A1 6/2013 Gross et al.

FOREIGN PATENT DOCUMENTS

| EP | 1964546 A1 | 9/2008 |
|---|---|---|
| JP | 2009167157 A | 7/2009 |
| JP | 2009167158 A | 7/2009 |
| JP | 2010018560 A | 1/2010 |
| JP | 2011026276 A | 2/2011 |
| JP | 2011026278 A | 2/2011 |
| JP | 2015168649 A | 9/2015 |

OTHER PUBLICATIONS

Fukuoka et al (J Oleo Sci, pp. 1-7, Apr. 20, 2015) (Year: 2015).*
Penn State Extension (Agronomy Facts 37: Adjuvants for Enhancing Herbicide Performance, 2009) (Year: 2009).*
Rau et al., "Downstream processing of mannosyierythritol lipids produced by Pseudozyma aphidis", European Journal of Lipids Science and Technology, vol. 107, 2005, pp. 373-380.
Anonymous, "PEG esters—Echem", Mar. 1, 2014, Retrieved from Internet: URL: http://web.archive.org/web/20140301052052/http://www.echem-group.com/product/peg-esters.
Anonymous, "Polyethyleneglycol Monostearate", May 20, 2006, Retrieved from Internet: URL: http://www.chemicalland21.com/specialtychem/perchem/POLYETHYLENEGLYCOLMONOSTEARATE.hi.
Dai Kitamoto et al., Microbial conversion of n-alkanes into glycolipid biosurfactants, marmosylerythritol lipids, by Pseudozyma (Candida antarctica), Biotechnology Letters, Springer Netherlands, NL, vol. 23, No. 20, Oct. 1, 2001, pp. 1709-1714.
International Search Report issued in International Patent Application No. PCT/EP2017/056465 dated May 18, 2017.
Joseph Irudayaraj Arutchelvi et al., "Mannosylerythritol lipids: a review", Journal of Industrial Microbiology & Biotechnology; Official Journal of Society for Industrial Microbiology, Springer, Berlin, DE, vol. 35, No. 12, Aug. 21, 2008, pp. 1559-1570.
Mnif Inès et al., "Glycolipid biosurfactant Potential related biomedical and biotechnological applications", Carbohydrate Research, vol. 416, Oct. 1, 2015, pp. 59-69.
N. Lourith et al., "Natural surfactants used in cosmetics: glycolipicis", International Journal of Cosmetic Science, vol. 31, No. 4, Aug. 1, 2009, pp. 255-261.
Tokuma Fukuoka et al., "Application of Yeast Glycolipid Biosurfactant, Mannosylerythritol Lipid, as Agrospreders", Journal of Oleo Science, vol. 64, No. 6, Jan. 1, 2015, pp. 689-695.

* cited by examiner

*Primary Examiner* — Craig D Ricci
(74) *Attorney, Agent, or Firm* — Arent Fox LLP

(57) ABSTRACT

The present invention relates to a concentrate comprising at least one lipid of mannosylerythritol and at least one ester of fatty acid and polyethylene glycol having an HLB value greater than or equal to 12, to the method for producing same and to the uses thereof, in particular as a surfactant.

12 Claims, 4 Drawing Sheets

Figure 1:
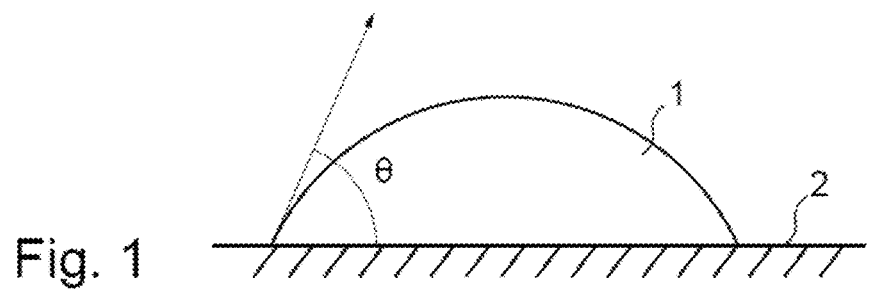

CONCENTRATE COMPRISING A MEL AND A POLYETHYLENE GLYCOL FATTY ACID ESTER HAVING AN HLB VALUE GREATER THAN OR EQUAL TO 12

CROSS REFERENCE TO RELATED APPLICATIONS

This application is a 35 U.S.C. 371 National Phase of PCT Application No. PCT/EP2017/056465 filed Mar. 17, 2017, which claims the benefit to FR Application No. 1652288 filed Mar. 17, 2016, the disclosure of which is hereby incorporated by reference in its entirety.

The present invention relates to a concentrate, to compositions comprising it, and to an emulsion comprising it. The present invention also relates to a process for the preparation of the concentrate, of the compositions, and of the emulsion according to the invention, and the use of the concentrate, in particular as surfactant, and more particularly as emulsifying agent.

The surfactants find an application in numerous fields. It is known in particular to use surfactants in the cleaning industry, for example in the preparation of products for household maintenance or cleaning, or also in the cosmetics industry. The use of surfactants is also of particular interest in the agricultural industry, in particular for the protection of plants. In the latter, the surfactants, and more particularly the emulsifying agents are generally used in the preparation of phytosanitary products, such as phytosanitary mixtures, such as for example herbicides, fungicides, insecticides, algicides or also products for stimulating the defences of plants. These phytosanitary products are often presented in the form of an emulsion in order to cause a preferred solvent, namely water, to co-exist together with generally hydrophobic active ingredients. In this case, the surfactant(s) present in these products also has/have an emulsifying property.

As well as their surfactant and optionally emulsifying properties these agents can have other properties. By way of example, in the context of a phytosanitary use, such an agent can also have a penetrating, moistening and/or wetting property. A surfactant, and more particularly an emulsifying agent having a wetting property promotes the spreading and the retention of the emulsion comprising it on crops. This results, on the one hand, in a reduction of the quantity of phytosanitary emulsion to be sprayed on the crops, and on the other hand, in an improvement in the effectiveness of the phytosanitary emulsions. The use of surfactants having emulsifying and wetting properties thus allows a reduction in the efforts and costs associated with the treatment of crops.

Moreover, whatever the types of industry in which they are used, it is preferable that the surfactants are environmentally friendly and are less toxic for the operators. This is particularly important when they are used in the preparation of phytosanitary emulsions, as these are generally spread over crops in significant quantities so that it is preferable, or even necessary, that the surfactants are ecologically advantageous, and in particular biodegradable.

More particularly, it would be useful to develop surfactants:
having an excellent surfactant, and more particularly emulsifying property,
making it possible to obtain stable emulsions,
having a good ability to increase the wetting power of the emulsions comprising them, such as phytosanitary emulsions, and
which would moreover be environmentally friendly.

The work of the inventor has made it possible to demonstrate that a specific concentrate had all of the advantageous properties described above.

The invention therefore relates to a concentrate comprising:
at least one mannosylerythritol lipid, and
at least one polyethylene glycol fatty acid ester having an HLB value greater than or equal to 12.

According to the invention, a "mannosylerythritol lipid" (also called "MEL") is a surfactant belonging to the class of glycolipids. More particularly, a MEL is an amphiphilic molecule the hydrophilic part of which is formed by a mannosylerythritol residue, and the hydrophobic part of which is formed by at least one fatty acid.

More particularly, by "MEL", is meant a molecule having the following general formula (I):

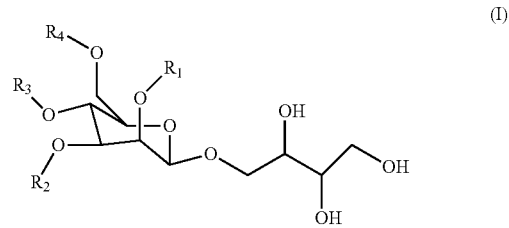

in which:
$R_1$ and $R_2$, identical or different, represent an unsaturated or saturated fatty acid, and
$R_3$ and $R_4$, identical or different, represent an acetyl group or a hydrogen atom.

Preferably, in the present invention, by "MEL", is meant a molecule having the following formula (II):

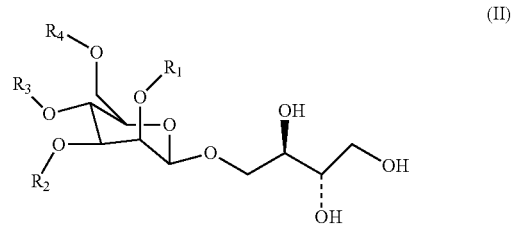

in which:
$R_1$ and $R_2$, identical or different, represent an unsaturated or saturated fatty acid, and
$R_3$ and $R_4$, identical or different, represent an acetyl group or a hydrogen atom.

The formulae (I) and (II) above can represent several molecules, each molecule therefore being a MEL. By "MELs", is meant at least two different molecules of formulae (I), and more particularly of formula (II).

The MELs are generally classified in four classes of molecules, denoted A to D, according to their degree of acetylation in positions $R_3$ and $R_4$. The class of the MELs-A comprises the molecules of formulae (I) or (II) having two acetyl groups in positions $R_3$ and $R_4$. The class of the MELs-B and the class of the MELs-C comprise the molecules of formulae (I) or (II) having a single acetyl group in positions $R_4$ and $R_3$ respectively. Finally, the class of the MELs-D comprises the molecules of formulae (I) or (II) not having an acetyl group ($R_3=R_4=H$).

As well as by their degree of acetylation, the MELs can vary in their structure, by the nature of the fatty acids which comprise their hydrophobic part. This variation is generally a function of the process implemented for obtaining the MELs.

The MELs are generally obtained by processes implementing the culture of fungi, and more particularly of yeasts.

Advantageously, the MELs to which the present application relates are obtained by a fermentation process, comprising the following steps:
  culturing a fungal strain and more particularly a yeast strain in the presence of a carbon source in order to obtain MELs; and
  recovering the MELs thus obtained.

The strains from which it is possible to obtain MELs are well known to a person skilled in the art. By way of example, it is known to use fungal strains of the genus *Pseudozyma* or of the genus *Ustilago*, in order to obtain MELs.

Advantageously, the strains used in the fermentation process described above, making it possible to obtain MELs, are fungal strains belonging to the genus *Pseudozyma*. Preferably, the strain is *Pzeudozyma antartica* or *Pzeudozyma aphidis*.

Such strains are usually cultured in a reactor in a medium comprising glucose, water and/or salts (such as magnesium sulphate, monopotassium phosphate and/or ammonium nitrate).

Advantageously, the different components of the medium (glucose and strains in particular) are sterilized separately before introduction into the reactor.

The temperature of the medium is preferably comprised between 20 and 35° C., more preferentially between 25 and 30° C.

In the present application, all the value ranges are inclusive.

Advantageously, the carbon source allowing the production of MELs by the strain is an oil, such as a vegetable oil. Preferably, the source of carbon is a soya oil or even more preferentially a rapeseed oil. These oils are particularly rich in fatty acids comprising a carbon-containing chain with 18 carbon atoms, such as oleic, linoleic and/or linolenic acid, as well as, to a lesser degree, in fatty acids comprising a carbon-containing chain with 16 carbon atoms, such as in palmitic acid.

The recovery of the MELs following the culture step can comprise a step of separating the MELs from the other components of the medium. This step can be done by standard separation methods known to a person skilled in the art.

Advantageously, the recovery of the MELs can comprise one or more of the following separation methods:
  settling;
  evaporation of water or drying;
  filtration; and/or
  centrifugation.

The concentrate according to the invention also comprises at least one polyethylene glycol fatty acid ester having an HLB (Hydrophilic-Lipophilic Balance) value greater than or equal to 12.

In the context of the present application, by "polyethylene glycol", also called "PEG", is meant a polymer of ethylene oxides having a molar mass of less than 20,000 g·mol$^{-1}$.

According to the invention, a polyethylene glycol fatty acid ester is a non-ionic surfactant.

The HLB value makes it possible to define, and in particular to quantify, the balance between the hydrophilic part and the lipophilic part of a surfactant molecule, this balance being linked to the solubility of the surfactant in water. The HLB value can vary from 0 to 20. The higher the HLB value, the greater the solubility of the surfactant in water.

In the context of the present application, the calculation of the HLB is carried out by Griffin's method:

$$HLB = 20 \times \frac{\text{Molecular mass of the hydrophilic part}}{\text{Molecular mass of the molecule}}$$

Preferentially, the polyethylene glycol fatty acid ester comprised in the concentrate according to the invention has an HLB value comprised between 12 and 20, more preferentially between 12 and 16 and even more preferentially comprised between 12 and 14.

Advantageously, the polyethylene glycol comprised in the polyethylene glycol fatty acid ester has a molar mass comprised between 200 and 4000 g·mol$^{-1}$, preferably comprised between 300 and 1400 g·mol$^{-1}$, more preferentially comprised between 400 and 800 g·mol$^{-1}$.

Advantageously, the fatty acid comprised in the polyethylene glycol fatty acid ester has a carbon-containing chain comprising between 8 and 24 carbon atoms, preferably between 16 and 20 carbon atoms.

A particularly preferred polyethylene glycol fatty acid ester according to the invention is polyethylene glycol-600 mono-oleate, such as that marketed by OLEON NV under the trade mark RADIA® 7404.

Throughout the present application, when a number is indicated behind the term "polyethylene glycol-" or "PEG-", this number corresponds to the molar mass of said polyethylene glycol.

More particularly, the invention relates to a concentrate comprising:
  at least one mannosylerythritol lipid, and
  at least one polyethylene glycol fatty acid ester having an HLB value greater than or equal to 12,
  in which the MEL:polyethylene glycol fatty acid ester ratio is comprised between 0.01 and 5.

The concentrate according to the invention has a surfactant property, and more particularly when it is placed in the presence of a hydrophobic liquid and water, the concentrate according to the invention allows the formation of an emulsion.

In fact, the concentrate according to the invention has excellent surfactant and/or emulsifying properties, as when it is added to a hydrophobic liquid and to water, the concentrate according to the invention allows the formation of an emulsion:
  uniform, and
  spontaneously.

By "spontaneously", is meant that only gentle stirring is required in order to obtain an emulsion. By way of example of gentle stirring, the container into which the concentrate according to the invention, the water and the hydrophobic liquid are added can be turned over manually so as to turn through an angle of 180° C., then returned to its initial position, according to what is indicated in step (i) of the standard CIPAC MT 36.3 ("*CIPAC method* 2000. *Prepared by the German Formulation Panel (DAPF). Chairman: G Menschel.*").

In the context of the present application, and unless stated otherwise, any reference made to a standard is a reference to the standard in force at the filing date.

The surfactant and more particularly the emulsifying properties of the concentrate according to the invention are more fully described in Example 2.

Moreover, when an emulsion is prepared from the concentrate according to the invention, it is stable over time.

Moreover, it has been demonstrated by the inventors that, surprisingly, an emulsion comprising the concentrate according to the invention has a high wetting power, and has a white colour that is particularly favourable to its use in various fields, such as for example in cosmetics. These characteristics are more fully described hereafter.

Moreover, the concentrate according to the invention is stable. By "stable", is meant that the concentrate shows no or shows little separation of phases after storage for 1 day, preferably 1 month, more preferentially 2 months.

Finally, the concentrate according to the invention has a good thickening property. By "thickening property", is meant that a concentrate according to the invention increases the viscosity of water. In other words, a composition comprising a concentrate according to the invention and water will have a viscosity greater than that of water alone, advantageously at least 200 mPa·s, preferably at least 500 mPa·s, more preferentially at least 800 mPa·s.

The concentrate according to the invention can therefore be used as thickening agent.

The stability and the thickening property of the concentrate according to the invention are more fully described in Example 9.

Advantageously the concentrate according to the invention comprises at least one alcohol having a number of carbon atoms comprised between 1 and 16.

By "alcohol", is meant more particularly a linear or branched alcohol. By "linear or branched", is meant that the cyclic alcohols are specifically excluded. Even more particularly, the alcohol is an alcohol constituted by a linear or branched hydrocarbon-containing chain, substituted by one or more hydroxyl (OH) group(s). By "hydrocarbon-containing chain", is meant a chain constituted only by carbon and hydrogen atoms, the hydrocarbon-containing chain then comprising between 1 and 16 carbon atoms. In other words, the alcohol does not comprise a heterosubstituent other than the hydroxyl group(s).

The alcohol(s) comprised in the concentrate according to the invention also make it possible to improve the stability and the wetting power of the emulsions formed from this concentrate.

Preferably, the total quantity of alcohol(s) in the concentrate according to the invention is comprised between 5 and 80% by weight, with respect to the total weight of the concentrate.

By total quantity of alcohol(s) present in the concentrate, is meant the quantity of molecule(s) of alcohol(s) present in said concentrate, the molecules of alcohol being as defined above.

Preferably, the total quantity of alcohol(s) is comprised between 10 and 75% by weight, more preferentially between 15 and 50% by weight, with respect to the total weight of the concentrate.

Advantageously, the alcohol is saturated.

The alcohol(s) are therefore linear or branched. As linear alcohols, heptanol (or heptan-1-ol), octanol (also called octan-1-ol or caprylic alcohol), lauric alcohol or nonanol (or nonan-1-ol or pelargonic alcohol) may be mentioned. As branched alcohols, octan-2-ol, 2-ethyl-hexanol, 7-methyl-octan-1-ol or 6-methyl-pentan-1-ol may be mentioned.

Advantageously the alcohol(s) comprised in the concentrate according to the invention have a hydrocarbon-containing chain comprising a number of carbon atoms comprised between 4 and 14, preferentially between 6 and 12.

Preferably, the alcohol(s) are selected from the alcohols having a hydrocarbon-containing chain comprising 8 to 10 carbon atoms or mixtures thereof. In particular, they are octanol, octan-2-ol, 2-ethyl-hexanol and/or lauric alcohol, preferably octan-2-ol.

Advantageously, the alcohol can be obtained from renewable sources, such as from animal fats or vegetable oils.

Favourably, the MEL:polyethylene glycol fatty acid ester ratio in the concentrate according to the invention is comprised between 0.01 and 5.

Preferably, the MEL:polyethylene glycol fatty acid ester ratio is comprised between 0.1 and 2, more preferentially between 0.5 and 2.

Advantageously, in the concentrate according to the invention, the total quantity of MEL(s) is comprised between 1 and 90% by weight, with respect to the total weight of the concentrate.

By total quantity of MEL(s) present in the concentrate, is meant the quantity of molecule(s) of MEL(s) of formulae (I) or (II) present in said concentrate.

Preferably, the total quantity of MEL(s) is comprised between 5 and 75% by weight, more preferentially between 10 and 50% by weight, even more preferentially between 15 and 45% by weight, with respect to the total weight of the concentrate.

Advantageously, the total quantity of polyethylene glycol fatty acid ester(s) in the concentrate according to the invention is comprised between 1 and 90% by weight, with respect to the total weight of the concentrate.

By total quantity of polyethylene glycol fatty acid ester(s) present in the concentrate, is meant the quantity of molecule(s) of polyethylene glycol fatty acid ester(s) present in said concentrate.

Preferably, the total quantity of polyethylene glycol fatty acid ester(s) is comprised between 5 and 75% by weight, more preferentially between 10 and 65% by weight, even more preferentially between 20 and 55% by weight, with respect to the total weight of the concentrate.

Advantageously, the concentrate according to the invention comprises at least two MELs selected from the group constituted by MEL-A, MEL-B, MEL-C and MEL-D.

Preferably, the concentrate according to the invention comprises MEL(s)-A, MEL(s)-B, MEL(s)-C and optionally MEL(s)-D, more preferentially MEL(s)-A, MEL(s)-B, MEL(s)-C and MEL(s)-D.

Advantageously, the concentrate according to the invention comprises MELs-A and MELs-B at a content comprised between 50 and 90% by weight, preferably comprised between 60 and 85% by weight, the percentages by weight being indicated with respect to the weight of the total quantity of MELs.

The concentrate according to the invention can also comprise MELs-C at a content greater than or equal to 5% by weight, preferably greater than or equal to 10% by weight, the percentages by weight being indicated with respect to the weight of the total quantity of MELs.

More particularly, the concentrate according to the invention can comprise MELs-A and MELs-B at a content comprised between 60% and 75% by weight, and MELs-C at a content greater than or equal to 20% by weight, the percentages by weight being indicated with respect to the weight of the total quantity of MELs.

The concentrate according to the invention can also comprise at least one free fatty acid and/or at least one triglyceride.

By "free fatty acid", is meant any fatty acid molecule that is not bound to another molecule. By "fatty acid", is meant any fatty acid molecule bound to another molecule, for example when this fatty acid molecule is present in a triglyceride or in a MEL.

The at least one free fatty acid and/or at least one triglyceride can have been introduced concomitantly with the at least one MEL.

In fact, depending on the process for obtaining the MELs, such as the fermentation process described above, and in particular depending on the separation method(s) implemented in the recovery step, the latter can comprise one or more free fatty acid(s) and/or triglyceride(s).

For example, the quantity of free fatty acid(s) and/or of triglyceride(s) present in the concentrate according to the invention can be comprised between 0.1 and 50% by weight, preferably between 0.01 and 40% by weight, with respect to the total weight of the concentrate.

More particularly, the concentrate comprises at least one free fatty acid and at least one triglyceride. In this case, the quantity of free fatty acid(s) and triglyceride(s) present in the concentrate according to the invention can be comprised between 0.01 and 50% by weight, preferably between 0.01 and 40% by weight, more preferentially between 1 and 35% by weight, with respect to the total weight of the concentrate.

Advantageously, the free fatty acid(s) comprise a carbon-containing chain comprising between 14 and 24 carbon atoms, preferably 16 or 18 carbon atoms.

Advantageously, the triglyceride(s) comprise fatty acids comprising a carbon-containing chain comprising between 14 and 24 carbon atoms, preferably 16 or 18 carbon atoms.

More particularly, in the present application, and in particular in the examples, when the MELs, at the end of the recovery step, comprise at least one free fatty acid, at least one triglyceride, water and/or strains, this mixture is called "mixture of MELs".

In this case, the free fatty acid(s) and/or triglyceride(s) can originate from the residual oil present with the MEL(s) at the end of the fermentation process described above, said residual oil being the oil utilized as a carbon source in the fermentation process, which has not been used by the strains. In addition, the free fatty acid(s) can originate from the metabolism, by the strains, of the triglycerides comprised in the oil utilized as a carbon source in said process.

Moreover, according to the process for obtaining MELs, such as the fermentation process described above, and in particular according to the separation method(s) implemented in the recovery step, the MELs can also comprise water and fungal strains, more particularly yeast strains.

According to a preferred embodiment of the concentrate according to the invention, it comprises a mixture of MELs having the following characteristics:
  a content of MELs greater than or equal to 40% by weight, preferably greater than or equal to 50% by weight, more preferentially greater than or equal to 55% by weight;
  a content of other components less than or equal to 60% by weight, preferably less than or equal to 50% by weight, more preferentially less than or equal to 45% by weight (including free fatty acids, triglycerides, water and/or strains),
the percentages by weight being given with respect to the total weight of the mixture of MELs.

Advantageously, in this preferred embodiment, the content of water and/or strains is less than 3% by weight, with respect to the total weight of the mixture of MELs.

This mixture of MELs can in particular be obtained according to the fermentation process described above.

An example of a mixture of MELs and the process for obtaining it is also described in the following publication:
  "*Downstream processing of mannosylerythritol lipids produced by Pseudozyma aphidis*"; Rau et al.; European Journal of Lipids Science and Technology 107 (2005) 373-380.

Preferably, a mixture of MELs comprises MELs of different classes, in general at least MELs-A, B and C. Preferentially, this mixture of MELs comprises MELs-A, B, C and D.

Moreover, a mixture of MELs advantageously comprises MELs-A and MELs-B at a content comprised between 50 and 90% by weight, preferably comprised between 60 and 85% by weight, the percentages by weight being indicated with respect to the weight of the total quantity of MELs.

In addition, a mixture of MELs advantageously comprises MELs-C at a content greater than or equal to 5% by weight, preferably greater than or equal to 10% by weight, the percentages by weight being indicated with respect to the weight of the total quantity of MELs.

More particularly, a mixture of MELs can comprise MELs-A and MELs-B at a content comprised between 60% and 75% by weight, and MELs-C at a content greater than or equal to 20% by weight, the percentages by weight being indicated with respect to the weight of the total quantity of MELs.

Such mixtures of MELs are for example obtained using a fermentation process such as those described above.

It is also possible to obtain a mixture of MELs having a content of MELs greater than or equal to 95%, preferably greater than or equal to 98% by weight, with respect to the total weight of the mixture of MELs. This mixture of MELs can, for example, be obtained using the fermentation process described above to which a purification step is added, at the end of the recovery step. This purification step can comprise a liquid/liquid extraction and/or passing over a mineral substrate. Passing over a mineral substrate can be a chromatography, such as an adsorption chromatography on a silica column, carried out using suitable solvents. Such solvents are known to a person skilled in the art.

According to a preferred alternative embodiment of the concentrate according to the invention, it can therefore also comprise a mixture of MELs which has the following characteristics:
  a content of MELs greater than or equal to 95% by weight, preferably greater than or equal to 98% by weight,
the percentages by weight being given with respect to the total weight of the mixture of MELs.

Moreover, the purification step, following the recovery step of the MELs, can be carried out so as to obtain one class of MELs or even one MEL, at a content greater than or equal to 50%. By way of example, this purification step can comprise a liquid/liquid extraction and/or passing over a mineral substrate (such as a chromatography), as defined above.

The invention also relates to a process for the preparation of a concentrate according to the invention, comprising a step of mixing at least one mannosylerythritol lipid and at least one polyethylene glycol fatty acid ester.

The concentrates according to the invention are easily prepared, by simple mixing of the components.

Advantageously, the mixing is carried out at ambient temperature under normal temperature and pressure (NTP) conditions.

Preferably, during the mixing, the components are heated at a temperature comprised between 25 and 55° C., more preferentially between 30 and 50° C., even more preferentially between 35 and 45° C.

Heating the components can allow a better homogenization of the concentrate according to the invention.

Optionally, prior to mixing, the process for the preparation of a concentrate according to the invention comprises obtaining at least one MEL, such as it is described above.

Advantageously, the MEL(s) are as described above and can be obtained by the fermentation process of MEL(s) described above, optionally followed by a purification step.

Advantageously, the polyethylene glycol fatty acid ester(s) used in the process have the characteristics as described above.

The mixing step of the process according to the invention can include an alcohol having a number of carbon atoms comprised between 1 and 16.

Advantageously, the alcohol(s) having a number of carbon atoms comprised between 1 and 16 have the characteristics as described above.

The invention also relates to a composition comprising a concentrate according to the invention, and a hydrophobic liquid.

Preferably, the hydrophobic liquid is selected from methyl oleate, ethyl oleate, and the methyl or ethyl esters of vegetable oil fatty acids, such as the methyl or ethyl esters of rapeseed, soya, olive, sunflower, castor, palm and/or linseed oil fatty acids, or mixtures thereof.

Preferably, the hydrophobic liquid is selected from the methyl or ethyl esters of rapeseed and/or olive oil fatty acids. More preferentially, the hydrophobic liquid is selected from the fatty acid methyl esters.

Advantageously, the quantity of hydrophobic liquid in the composition according to the invention is comprised between 50 and 99% by weight, preferably between 65 and 98% by weight, even more preferentially between 80 and 96% by weight, with respect to the total weight of the composition.

The invention also relates to a process for the preparation of a composition according to the invention, comprising a step of mixing a concentrate according to the invention with a hydrophobic liquid.

Advantageously, the mixing is carried out at ambient temperature under normal temperature and pressure (NTP) conditions.

Preferably, during the mixing, the components are heated at a temperature comprised between 25 and 55° C., more preferentially between 30 and 50° C., even more preferentially between 35 and 45° C.

Heating the components can allow a better homogenization of the composition according to the invention.

Advantageously, the concentrate and the hydrophobic liquid have the preferred characteristics of these components as described above.

The invention also relates to a phytosanitary composition comprising a concentrate according to the invention, or a composition according to the invention, and a pesticide active ingredient.

Advantageously, the pesticide active ingredient is selected from the following active ingredients: herbicides, fungicides, insecticides, acaricides, growth regulators, insect repellents, biocontrol and/or plant defence stimulators.

Preferably, the pesticide active ingredient is a herbicide active ingredient, a fungicide active ingredient, an insecticide active ingredient and/or a plant defence stimulator active ingredient.

Advantageously, the phytosanitary composition according to the invention comprises:
one or more fungicide active ingredients such as a carboxamide, a strobilurin, an azole (triazole, imidazole), a heterocyclic compound (pyridine, pyrimidine, piperazine, morpholine), a carbamate, an essential oil (cinnamaldehyde, thymol, tea oil), a micro-organism (fungi such as *Gliocladium catenulatum*, yeasts, bacteria such as *Bacillus subtilis*) other than those capable of being comprised in the mixture of MELs described above, a polysaccharide (chitosan) and/or, one or more herbicide active ingredients such as a lipid biosynthesis inhibitor, an acetolactase synthase inhibitor (also called "ALS inhibitor"), a photosynthesis inhibitor, an acetamide, a derivative of amino acids such as an organophosphorus-containing derivative of amino acid (glufosinate or glyphosate) or salts thereof (ammonium salts of glufosinate, mono or di ammonium, potassium, isopropylamine salts of glyphosate), an aryloxyphenoxyproprionate, bipyridyl, cyclohexanedione, a dinitroaniline, diphenyl ether, hydroxybenzonitrile, imidazolinone, a phenoxy acetic acid, pyrazine, pyridine, a sulphonylurea, a triazine, a urea, a carbamate, a fatty acid of natural origin having a herbicide activity (caprylic acid, pelargonic acid) or derivatives thereof (salts, soaps), and/or one or more insecticide active ingredients such as an organo(thio)phosphate, a carbamate, a pyrethroid, a growth regulator of insects, an agonist/antagonist of the nicotinic receptors, an antagonist of GABA, a macrocyclic lactone, geraniol, eugenol, thymol, neem oil, and/or one or more plant defence stimulator active ingredients, such as *Bacillus subtilis*, a derivative of jasmonic acid, an alga extract.

The phytosanitary composition according to the invention can be stored for a long time before use, without reducing its pesticide active ingredient content. In fact, the active ingredient content in the composition according to the invention reduces very little over time, even after storage for several months. This effect is more fully described in Example 6.

Advantageously, the pesticide active ingredient is of natural origin. Such pesticide active ingredients are generally called bio-pesticide active ingredients or biocontrol active ingredients.

Moreover, it will be noted that the active ingredient comprised in the phytosanitary composition according to the invention can have at the same time several of the following properties: herbicide, fungicide, insecticide, acaricide, growth regulator, insect repellent and/or plant defence stimulator.

Advantageously, the quantity of pesticide active ingredient is comprised between 0.1 and 30% by weight, preferably between 1 and 20% by weight, more preferentially between 5 and 15% by weight with respect to the total weight of the phytosanitary composition.

The invention also relates to a cosmetic composition comprising a concentrate according to the invention, or a composition according to the invention, and a cosmetic active ingredient.

Advantageously, the cosmetic composition comprises one or more cosmetic active ingredient(s) selected from:
a moisturizer such as jojoba oil, sweet almond oil, paraffin, wheat germ oil, collagen, pectin, chitosan, a glycosaminoglycan, and/or an organic UV filter such as PABA, PARA, a salicylate, a cinnamate, an anthranilate, benzophenone-3, butyl methoxydibenzoylethane, ethylhexyl triazone, dometrizol trisiloxane, diethylhexyl butamido triazone, 4-methylbenzylidene camphor, bemotrizinol, diethylamino hydroxybenzoyl hexyl benzoate, phenyl salicylate, methylene bis-benzotriazolyl tetramethylbutylphenol, benzophenone-1, benzophenone-2, benzophenone-8, bis-ethylhexyloxyphenol methoxyphenyl triazine, or a mineral UV filter, and/or an anti-ageing agent such as a retinoid, an α- or β-hydroxy acid, a water-soluble vitamin, ascorbyl palmitate, a ceramide, a pseudo ceramide, a phospholipid, cholesterol, a sterol and/or, an anti-cellulite agent such as isobutylmethylxanthine, theophylline, and/or an anti-acne agent such as resorcinol, resorcinol acetate, benzoyl peroxide, salicylic acid, azelaic acid, and/or a firming agent such as a plant extract (linseed extract), rose water, and/or a vitamin such as vitamin A, derivatives thereof, vitamin B2, pantothenic acid, vitamin D, vitamin E.

Advantageously, the quantity of cosmetic active ingredient is comprised between 0.1 and 30% by weight, preferably between 0.5 and 20% by weight, more preferentially between 1 and 15% by weight with respect to the total weight of the cosmetic composition.

The invention also relates to a process for the preparation of a phytosanitary composition or of a cosmetic composition according to the invention, comprising a step of mixing a concentrate according to the invention, or a composition according to the invention, with an active ingredient.

More particularly:

In the context of the preparation of a phytosanitary composition, the process according to the invention comprises a step of mixing a concentrate according to the invention, or a composition according to the invention, with a pesticide active ingredient;

In the context of the preparation of a cosmetic composition, the process according to the invention comprises a step of mixing a concentrate according to the invention, or a composition according to the invention, with a cosmetic active ingredient.

Advantageously, the components used in these preparation processes have the preferred characteristics of these components as described above.

Moreover, the invention relates to an emulsion comprising a composition according to the invention, a phytosanitary composition according to the invention or a cosmetic composition according to the invention, and water.

When an emulsion is prepared from a composition according to the invention, from a phytosanitary composition according to the invention, or from a cosmetic composition according to the invention, which comprise a concentrate according to the invention, it is stable over time. By "stable", is meant that the emulsion shows no or shows little separation of phases after storage for 30 seconds, preferably 30 minutes, more preferentially 2 hours, even more preferentially 24 hours. Advantageously, the stability of an emulsion prepared from the concentrate according to the invention is characterized according to step (ii) of the standard CIPAC MT 36.3.

The stability of emulsions prepared from compositions according to the invention comprising a concentrate according to the invention is more fully described in Example 3.

In addition, it has been demonstrated by the inventors that, surprisingly, an emulsion prepared from a composition comprising the concentrate according to the invention has a high wetting power. Thus, when an emulsion prepared from a composition comprising the concentrate according to the invention is applied to a solid surface (such as a hydrophobic flat surface), the wetting of this solid surface by this emulsion is high (see Example 4).

In the context of the present application:

by "wetting", is meant the spreading ability of a liquid over a solid;

by "surface tension" of a liquid, is meant the force exerted at the interface between this liquid and a solid.

by contact angle of a drop of liquid 1 deposited on a flat solid surface 2, is meant the angle θ formed by the tangent to the drop of liquid 1 at the point of contact with the flat solid surface 2, as shown in FIG. 1.

By way of example, when a liquid, such as a drop of solution or of emulsion, and a solid, such as a plant wall or leaf, are placed in contact, the ability of the liquid to wet the solid, i.e. to spread or become distributed over it, will depend directly of the force exerted at the interface between liquid and solid, which is generally defined as the surface tension. The surface tension therefore represents the force making it possible for the liquid to adhere to the solid, or preventing it becoming distributed over it. Thus the higher surface tension, the less the liquid is capable of wetting the solid in question.

Figure 2A:
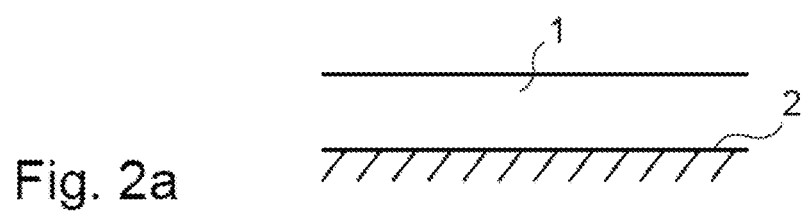
Figure 2B:
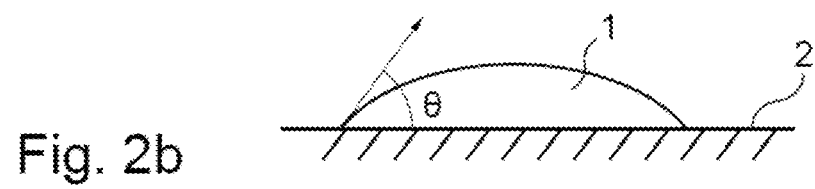
Figure 2C:
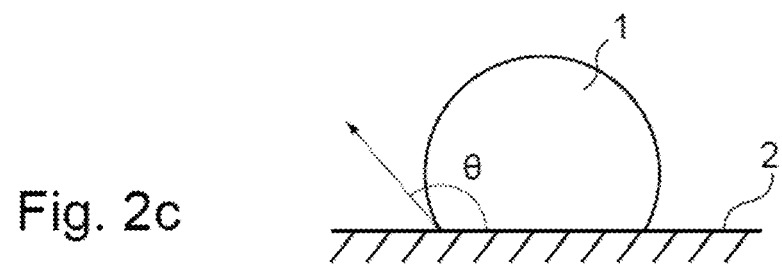

Several cases in point can therefore be shown in order to illustrate the idea of wetting. FIGS. 2a to 2c represent more particularly three cases in point.

Thus, as shown in FIG. 2a, when a drop of liquid 1 falls onto a flat solid surface 2, it can achieve a total wetting of this surface 2, i.e. become distributed over the entire surface thereof, by forming a film with a contact angle θ equal to 0 with said surface 2. Alternatively, the drop 1 can partially wet the surface 2 (FIG. 2b), i.e. it does not become totally distributed over the latter, by forming a drop with a contact angle θ comprised between 0 and 90° with said surface 2. Finally, the drop 1 may not wet the surface 2 at all (FIG. 2c), i.e. it does not become distributed over it, by forming a drop with a contact angle θ greater than 90° with said surface 2.

Moreover, an emulsion comprising the composition according to the invention has the advantage of being able to be sprayed in the form of droplets with a diameter advantageously greater than 100 μm, which makes it possible to reduce the phenomenon of drift during spraying.

Moreover, an emulsion prepared from the composition according to the invention comprising the concentrate according to the invention has a white colour which is particularly favourable for its use in various fields, such as for example in cosmetics. This characteristic is more particularly demonstrated in FIG. 3.

The water is chosen depending on the composition from which the emulsion is prepared.

For example, in the context of an emulsion comprising a phytosanitary composition according to the invention, the water is of the type of that used in the preparation of phytosanitary emulsions, such as a drill water, which can be a water having a hardness from medium to hard. Advantageously, the water having a hardness from medium to hard has a hardness comprised between 300 and 600 ppm, preferentially between 450 and 550 ppm. Such a solution is generally intended to be sprayed, for example by a farmer on crops.

In the context of an emulsion comprising a cosmetic composition according to the invention, the water is a water generally used in cosmetics, such as a distilled water or a water treated by reverse osmosis.

Advantageously the quantity of composition, phytosanitary composition or cosmetic composition according to the invention in the emulsion according to the invention is comprised between 0.001 and 20% by weight, preferably between 0.005 and 15% by weight, even more preferentially between 0.01 and 10% by weight, with respect to the total weight of the emulsion.

Preferably, the quantity of water in the emulsion according to the invention is comprised between 50 and 99.99% by weight, preferably between 80 and 99.9% by weight, more preferentially between 85 and 99.9% by weight, with respect to the total weight of the emulsion.

In particular, the quantity of water can be comprised between 90.0 and 99.5% by weight, with respect to the total weight of the emulsion.

Advantageously, the emulsion according to the invention is an oil (or hydrophobic liquid)-in-water emulsion.

The invention also relates to a process for the preparation of an emulsion according to the invention, comprising a step of mixing a composition according to the invention, a phytosanitary composition according to the invention, or a cosmetic composition according to the invention, with water.

The invention also relates to the use of a concentrate according to the invention, as surfactant.

In particular, the concentrate according to the invention can be used as emulsifier.

The concentrate according to the invention can be used in all the known applications of surfactants, and more particularly of emulsifiers.

The concentrate according to the invention can be used as surfactant in the preparation of any type of solutions in which it is usual to use surfactants. By "solution", in the present application, is meant any composition comprising water such as, for example, an emulsion, a dispersion or a suspension. By way of example, the concentrate according to the invention can be used in cleaning solutions, such as solutions for household maintenance.

Advantageously, the concentrate according to the invention is used as surfactant in a phytosanitary solution, such as a pesticide solution.

Moreover, the concentrate according to the invention can be used as surfactant in a cosmetic solution.

Moreover, a concentrate according to the invention can be used in various other applications, such as in fire pumps.

The invention also relates to the use of a concentrate according to the invention as thickening agent.

The concentrate according to the invention is advantageously used as thickening agent in cosmetics.

Finally, the invention relates to the use of a concentrate or of a composition according to the invention as adjuvant.

Preferably, the adjuvant has a wetting property.

Figure 3:
Figure 4:
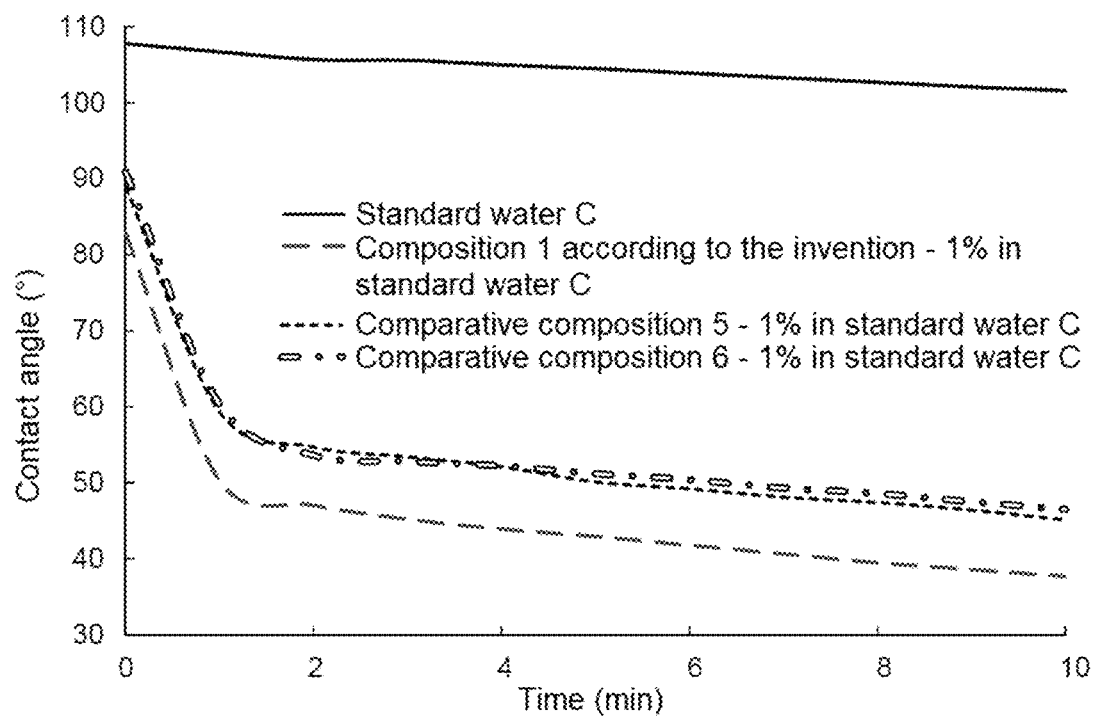
Figure 5:
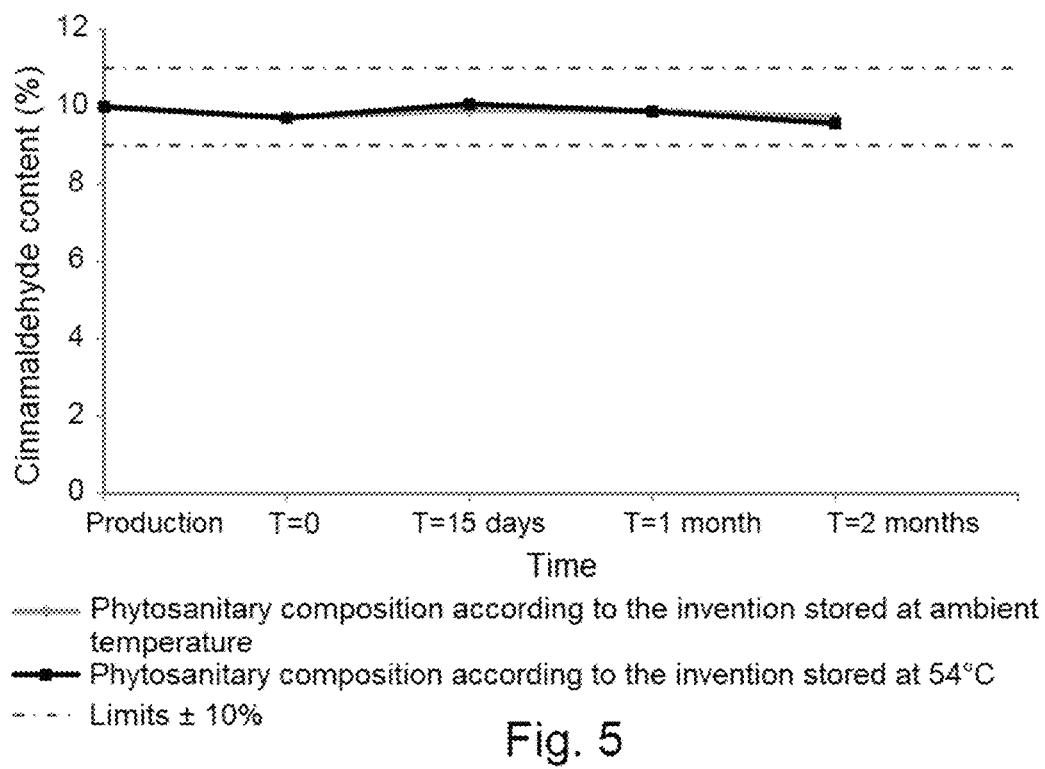
Figure 6:
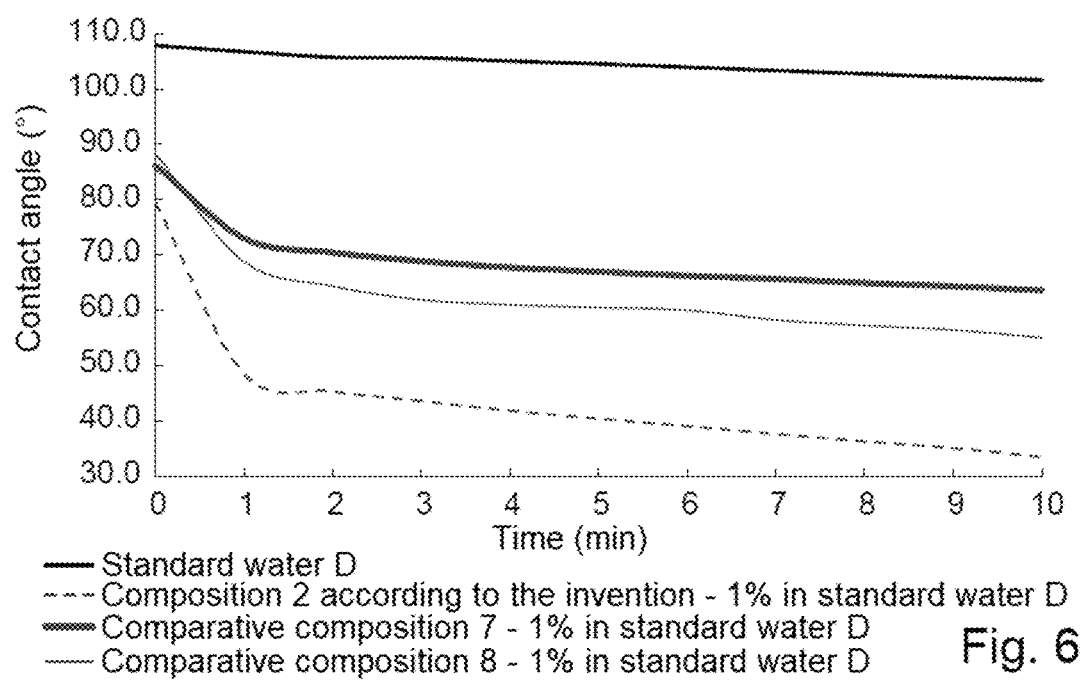

The invention will be better understood in light of the examples which follow, given by way of illustration, with reference to the following figures:

FIG. 1, which represents the contact angle θ formed by the tangent to a drop of liquid 1 at the point of contact with a flat solid surface 2;

FIG. 2, which represents three cases in point showing the idea of wetting, namely the case of a total wetting of a flat solid surface 2 by a drop of liquid 1 (FIG. 2a), the case of a partial wetting of a flat solid surface 2 by a drop of liquid 1 (FIG. 2b), and the case where a drop of liquid 1 does not wet a flat solid surface 2 (FIG. 2c);

FIG. 3, which is a photograph of an emulsion comprising a concentrate according to the invention (bearing the number 1 in the photograph) and of an emulsion comprising a comparative concentrate (bearing the number 3 in the photograph);

FIG. 4, which is a diagram representing the reduction in the contact angle obtained with an emulsion prepared from a composition according to the invention (comprising a concentrate according to the invention), and with emulsions comprising comparative compositions (comprising comparative concentrates);

FIG. 5, which is a diagram representing the change in the content of pesticide active ingredient over time of a phytosanitary composition according to the invention, and FIG. 6, which is a diagram representing the reduction in the contact angle obtained with an emulsion prepared from a composition according to the invention (comprising a concentrate according to the invention), and with emulsions comprising comparative compositions (comprising comparative concentrates).

EXAMPLE 1: PREPARATION OF CONCENTRATES ACCORDING TO THE INVENTION

1. Obtaining the MELs

The MELs were obtained by a fermentation process comprising the following steps:
culturing a yeast strain such as *Pseudozyma aphidis* in the presence of vegetable oil (rapeseed) in order to obtain the MELs; and
recovering the MELs thus obtained.

At the end of the step of recovering the MELs, a mixture of MELs 1A is obtained, which has the following characteristics:
Content of MELs: 55% by weight
Content of other components: 45% by weight (of which 42% by weight free fatty acids and triglycerides and 3% by weight water and strain),
the percentages by weight being given with respect to the total weight of the mixture of MELs obtained.

In particular, the mixture of MELs 1A comprises MELs-A at a content of 52% by weight, MELs-B at a content of 12% by weight, MELs-C at a content of 35% by weight, and MELs-D at a content of 1% by weight, the percentages by weight being given with respect to the weight of the total quantity of MELs.

2. Polyethylene Glycol Fatty Acid Ester

Polyethylene glycol-600 mono-oleate ("PEG-600-oleate") marketed by OLEON NV under the trade mark RADIA® 7404 was used.

3. Alcohol 2-octanol (Sigma-Aldrich) was used.

4. Process for the Preparation of Concentrates According to the Invention

Concentrate 1

57% by weight of the mixture of MELs and 43% by weight of Radia® 7404 were added into a 60 ml glass flask, the percentages by weight being indicated with respect to the total weight of the concentrate obtained, then stirred manually until homogenization of the concentrate was achieved. During stirring, it is possible to heat the concentrate at 40° C. in order to facilitate the homogenization.

Concentrate 2

40% by weight of the mixture of MELs, 30% by weight of 2-octanol and 30% by weight of Radia® 7404 were added into a 60 ml glass flask, the percentages by weight being indicated with respect to the total weight of the concentrate obtained, then stirred manually until homogenization of the concentrate was achieved. During stirring, it is possible to heat the concentrate at 40° C. in order to facilitate the homogenization.

EXAMPLE 2: EVALUATION OF THE SURFACTANT AND MORE PARTICULARLY THE EMULSIFYING PROPERTIES OF THE CONCENTRATES ACCORDING TO THE INVENTION AND OF COMPARATIVE CONCENTRATES

1. Materials and Methods
1.1 Material
The products which were used in this example are the following:
concentrates 1 and 2 according to the invention prepared in Example 1
polyethylene glycol-600 mono-oleate (Radia® 7404, OLEON NV, HLB=13.2)
the mixture of MELs prepared in Example 1
methyl esters of rapeseed oil fatty acids (Radia® 7955, OLEON NV)
standard water C (prepared according to the standard CIPAC MT 18.1)
The following equipment was also used in this Example:
60 mL glass flasks
100 mL graduated test tubes
5 mL graduated pipettes
1.2. Methods
Concentrates According to the Invention
Concentrates 1 and 2 prepared in Example 1 were used.
Preparation of Comparative Concentrates
Comparative Concentrate 3
Concentrate 3 comprises only Radia® 7404.
Comparative Concentrate 4
Concentrate 4 comprises only the mixture of MELs prepared in Example 1.
Evaluation of the Surfactant Properties of Concentrates 1 to 4
A protocol for the preparation of emulsions from concentrates 1 and 2 according to the invention and from comparative compositions concentrates 3 and 4 was carried out, according to step (i) of the standard CIPAC MT 36.3 ("*CIPAC method* 2000. *Prepared by the German Formulation Panel (DAPF). Chairman: G Menschel.*").
Firstly, concentrates 1 to 4 are brought into contact with a hydrophobic liquid according to the following protocol:
To this end:
7% by weight of concentrate 1 and 93% by weight of Radia® 7955 were added into a flask, the percentages by weight being indicated with respect to the total weight of the composition obtained, then stirred manually until homogenization of the composition was achieved. During stirring, it is possible to heat the composition at 40° C. in order to facilitate the homogenization.
10% by weight of concentrate 2 and 90% by weight of Radia® 7955 were added into a flask, the percentages by weight being indicated with respect to the total weight of the composition obtained, then stirred manually until homogenization of the composition was achieved. During stirring, it is possible to heat the composition at 40° C. in order to facilitate the homogenization,
3% by weight of concentrate 3 and 97% by weight of Radia® 7955 were added into a flask, the percentages by weight being indicated with respect to the total weight of the composition obtained, then stirred manually until homogenization of the composition was achieved. During stirring, it is possible to heat the composition at 40° C. in order to facilitate the homogenization,
4% by weight of concentrate 4 and 96% by weight of Radia® 7955 were added into a graduated test tube, the percentages by weight being indicated with respect to the total weight of the composition obtained, then stirred manually until homogenization of the composition was achieved. During stirring, it is possible to heat the composition at 40° C. in order to facilitate the homogenization.
In this way compositions 1 to 4 are obtained.
These compositions 1 to 4 are then brought into contact with water according to the following protocol:
1% by weight of the different compositions 1 to 7 were respectively added to 99% by weight of standard water in graduated test tubes, the percentages by weight being indicated with respect to the water-preparation mixture. The graduated test tubes were closed using a stopper. The graduated test tubes were then turned over once. According to note 4 of the standard CIPAC MT 36.3, when a test tube is "turned over once", it means that the graduated test tube is turned over manually so as to turn through an angle of 180° C., then returned to its initial position, the operation taking approximately two seconds.
After 30 seconds, it was observed with the naked eye whether an emulsion had formed or not in each test tube. When an emulsion had formed, it was observed whether it was uniform (complete), or on the other hand incomplete. When a uniform emulsion forms, this means that the concentrate has an excellent surfactant property. On the other hand, when the emulsion is incomplete, this means that the concentrate does not have a good surfactant property.
The results are presented in Table 1 below.

TABLE 1

Surfactant and emulsifying properties of concentrates 1 to 4

| Concentrate | Observation at 30 seconds |
|---|---|
| Concentrate 1 according to the invention | Uniform emulsion |
| Concentrate 2 according to the invention | Uniform emulsion |
| Comparative concentrate 3 | Uniform emulsion |
| Comparative concentrate 4 | No emulsion formed |

The results presented in Table 1 show that the concentrate according to the invention, when it is placed in the presence of water and a hydrophobic liquid, spontaneously allows the formation of uniform emulsions (after gentle stirring: a single manual turning). The concentrates according to the invention therefore have an excellent surfactant and more particularly emulsifying property.
Emulsions 1 to 3 prepared from concentrates 1 to 3 were used in Example 3 hereafter.

EXAMPLE 3: EVALUATION OF THE STABILITY OF EMULSIONS PREPARED FROM CONCENTRATES ACCORDING TO THE INVENTION AND FROM A COMPARATIVE CONCENTRATE

The stability of emulsions 1 to 3 prepared in Example 2 was evaluated, according to step (ii) of the standard CIPAC MT 36.3. When an emulsion is stable, it appears in the form of a single phase. On the other hand, when an emulsion is unstable, a separation of the oil phase and the aqueous phase can be observed with the naked eye. This separation of phases results in the presence of cream, which represents the aqueous phase during separation, and free oil, which represents the oil phase during separation. The level of separation of the oil phase and of the aqueous phase can be quantified by the volumes of cream and of free oil present in the emulsion. Moreover, the preparation of an emulsion can result in the formation of foam. On an industrial scale, the drawback of the formation of foam during the preparation of a phytosanitary emulsion is that the user is not able to pour the quantity of water required for the preparation of this emulsion, which can result in too high a concentration of phytosanitary active ingredient, or even in an overflowing of the tank containing the emulsion. The quantity of foam can be quantified by the volume of foam present in the emulsion.

Evaluation of the Stability of Emulsions 1 to 3

Following observation of emulsions 1 to 3 of Example 2 for 30 seconds, the test tubes containing these emulsions were turned over ten times then deposited in a room where they remained for 24 hours at a constant temperature of 20+/−2° C. At 30 minutes, at 1 hour, at 2 hours and at 24 hours, the volumes of free oil and/or of cream formed at the top or at the bottom of the emulsions, were measured by reading the corresponding volume on the graduated test tubes. The volumes of foam were also measured in the same way.

Results

The results are presented in Table 2 hereafter.

TABLE 2

Stability of emulsions 1 to 3

|  | Emulsion 1 | | | Emulsion 2 | | | Emulsion 3 | | |
| --- | --- | --- | --- | --- | --- | --- | --- | --- | --- |
|  | Foam (mL) | Cream (mL) | Oil (mL) | Foam (mL) | Cream (mL) | Oil (mL) | Foam (mL) | Cream (mL) | Oil (mL) |
| 30 minutes | 1 | 0 | 0 | 1 | 0 | 0 | 3 | 0.5 | 0 |
| 1 hour | 1 | 0 | 0 | 0.5 | 0 | 0 | 2 | 1 | 0 |
| 2 hours | 0 | 1 | 0.2 | 0.5 | 1 | 0 | 1 | 1 | 0 |
| 24 hours | 0 | 0 | 1 | 0 | 1 | 0 | 0 | 2 | 0 |

The results presented in Table 2 show that emulsions 1 and 2 according to the invention have a better stability than comparative emulsion 3. In particular, the appearance of cream in emulsions 1 and 2 according to the invention is less rapid than in comparative emulsion 3.

Moreover, emulsions 1 and 2 according to the invention comprise less foam than comparative emulsion 3.

In addition, by comparing emulsions 1 and 2, it is noted, after 24 h, that oil appears on the surface of emulsion 1 not comprising alcohol. This phenomenon is not observable for emulsion 2, which is of identical composition to emulsion 1 but which also comprises an alcohol. As a result, the latter allows better stabilization of the emulsion over time.

Moreover, an emulsion comprising a concentrate according to the invention has a very white colour, which makes it particularly suitable for a cosmetic use.

By way of example, the photographs of emulsion 1 comprising concentrate 1 according to the invention (bearing the number 1 in the photograph) and of emulsion 3 comprising comparative concentrate 3 (bearing the number 3 in the photograph) are shown in FIG. 3. These photographs were taken 5 minutes after turning the test tubes containing these emulsions ten times.

EXAMPLE 4: EVALUATION OF THE WETTING POWER OF EMULSIONS PREPARED FROM A CONCENTRATE ACCORDING TO THE INVENTION AND FROM COMPARATIVE CONCENTRATES

1. Materials and Methods
1.1. Material
The following products were used:
the mixture of MELs prepared in Example 1 ("MEL")
methyl esters of rapeseed oil fatty acids ("EMC" Radia® 7955, OLEON NV)
polyethylene glycol-600 mono-oleate ("PEG-600-oleate" Radia® 7404, OLEON NV)
polysorbate 20 (Radia® 7137, OLEON NV, HLB: 16.5)
polysorbate 80 (Radia® 7157, OLEON NV, HLB: 14.9)
standard water C
The following equipment was used:
glass flasks,
a 1 mL syringe provided with a needle with a diameter of 0.63 mm
a hydrophobic parafilm (Parafilm "M", NEENAH, Wis. 54956)
the goniometer DSA10 (KRUSS)
the "Drop shape analysis" software (KRUSS)
2. Methods
Preparations of Concentrate According to the Invention
Concentrate 1 of Example 1 was used.

Preparation of Comparative Concentrates

Comparative Concentrate 5

57% by weight of the mixture of MELs and 43% by weight of Polysorbate 20 were added into a 60 ml glass flask, the percentages by weight being indicated with respect to the total weight of the concentrate obtained, then stirred manually until homogenization of the concentrate was achieved. During stirring, it is possible to heat the concentrate at 40° C. in order to facilitate the homogenization.

Comparative Concentrate 6

57% by weight of the mixture of MELs and 43% by weight of Polysorbate 80 were added into a 60 ml glass flask, the percentages by weight being indicated with respect to the total weight of the concentrate obtained, then stirred manually until homogenization of the concentrate was achieved. During stirring, it is possible to heat the concentrate at 40° C. in order to facilitate the homogenization.

Preparation of Emulsions from Concentrates 1, 5 and 6

A protocol for the preparation of emulsions from concentrate 1 according to the invention and from comparative concentrates 5 and 6 was carried out, according to step (i) of the standard CIPAC MT 36.3 ("CIPAC method 2000. Prepared by the German Formulation Panel (DAPF). Chairman: G Menschel.").

To this end, firstly, concentrates 1, 5 and 6 are brought into contact with a hydrophobic liquid according to the following protocol:

7% by weight of the different concentrates 1, 5 and 6 and 93% by weight of Radia® 7955 were added into flasks, the percentages by weight being indicated with respect to the total weight of each composition obtained, then stirred manually until homogenization of the composition was achieved. During stirring, it is possible to heat the compositions at 40° C. in order to facilitate the homogenization. In this way compositions 1, 5 and 6 are obtained.

These compositions 1, 5 and 6 are then brought into contact with water according to the following protocol:

1% by weight of the different compositions 1, 5 and 6 obtained were respectively added to 99% by weight of standard water in flasks, the percentages by weight being indicated with respect to the total weight of the water-composition mixture. The flasks were closed using a stopper. The flasks were then turned over once. Emulsions 1, 5 and 6 were obtained.

Measurement of the Contact Angles

Contact angle measurements were carried out for each of emulsions 1, 5 and 6 and for the control solution, using the goniometer.

To this end, a drop of each emulsion or of the control solution (3 µL) was formed using the syringe. The syringe was then placed approximately 0.5 cm above the hydrophobic parafilm. By gravity, this drop became detached from the needle and fell onto the hydrophobic parafilm. The variation in the contact angle was monitored for 10 minutes from the moment when the drop touched the parafilm, using the analysis software.

The results were then processed in order to compare the variations in contact angles for each of emulsions 1, 5 and 6, with respect to the control solution 2. Results The results of the contact angle measurements for each of emulsions 1, 5 and 6 and for the control solution are presented in FIG. 4.

The results show that the reduction in the contact angle obtained with emulsion 1 is significantly greater than that obtained with each of emulsions 5 and 6.

EXAMPLE 5: USE OF A CONCENTRATE ACCORDING TO THE INVENTION IN THE PREPARATION OF A PHYTOSANITARY COMPOSITION—PREPARATION OF AN EMULSION CONTAINING AN ESSENTIAL OIL

Concentrate 2 according to the invention prepared in Example 1 was used in the preparation of a phytosanitary composition.

Concentrate 2 has the following characteristics:

| Components | % by weight* |
|---|---|
| Mixture of MELs | 40 |
| Radia ® 7404 | 30 |
| 2-octanol | 30 |

*Percentage by weight with respect to the total weight of the concentrate.

The phytosanitary composition was then prepared, by simple mixing of concentrate 2 according to the invention with the 3 other components described in the table hereafter. The phytosanitary composition according to the invention obtained has the following characteristics:

| Components | % by weight* |
|---|---|
| Concentrate 2 according to the invention | 10% |
| Radia ® 7955 | 79.95% |
| Cinnamaldehyde (Herbarom laboratoire) | 10% |
| Eugenol (Sigma-Aldrich) | 0.05% |

*Percentage by weight with respect to the total weight of the phytosanitary composition.

An emulsion was then prepared from the phytosanitary composition according to the invention obtained, as follows:

50% by weight of water, 1% by weight of the phytosanitary composition according to the invention, then 49% by weight of water were successively added into a resealable container, the percentages by weight being indicated with respect to the total weight of the water-composition mixture obtained. The container was then sealed then turned over in order to obtain the emulsion. If necessary, the pH and the salinity of the water will have been adjusted beforehand.

The emulsion according to the invention obtained has the following characteristics:

| Components | % by weight* |
|---|---|
| Phytosanitary composition according to the invention | 1% |
| Water | 99% |

*Percentage by weight with respect to the total weight of the emulsion.

EXAMPLE 6: EVALUATION OF THE CONTENT OF PESTICIDE ACTIVE INGREDIENT OVER TIME IN A PHYTOSANITARY COMPOSITION ACCORDING TO THE INVENTION

The change in the cinnamaldehyde content over time of the phytosanitary composition according to the invention prepared in Example 5 was analysed by gas chromatography (GC analysis).

1. Equipment

The following equipment was used:
a balance accurate to 0.00001 g
1 and 5 mL automatic pipettes
Pasteur pipettes
20 and 100 mL measuring flasks
a chromatograph for gas chromatography (GC 6580-Agilent Technologies)
a 5 µL syringe 2. Methods The phytosanitary composition according to the invention prepared in Example 5 was stored for two months during which a GC analysis was carried out at different times (production, 0 days, 15 days, 1 month, 2 months, 3 months).

The storage was carried out:
at ambient temperature (approximately 20° C. under normal temperature and pressure (NTP) conditions), or
at 54° C.

The parameters of the GC analysis are the following:
injector: split mode; temperature: 350° C.; split ratio: 10:1
mobile phase: Helium
carrier gas flow rate: 2 mL/min
analysis time: 36 minutes
injection volume: 2 µL
detector: FID; temperature: 250° C.; air: 450 mL/min; H2: 40 mL/min; He: 30 mL/min
column: DB5 HT 15 m*250 µm*0.1 µm All the components used in the preparation of the phytosanitary composition according to the invention were passed alone through GC according to the GC parameters above. This made it possible to verify that none of these components had a retention time identical to cinnamaldehyde or to the internal standard (azulene).

More particularly:

the retention time of cinnamaldehyde is 6 min.

the retention time of azulene is 6.7 min.

the components have retention times which are different to those of cinnamaldehyde and azulene.

The selectivity of the method is in compliance.

During a $1^{st}$ step, the internal calibration with solutions of cinnamaldehyde at different concentrations was carried out.

Then, the $2^{nd}$ step consisting of the GC analysis was carried out, followed by calculation of the level of cinnamaldehyde in the phytosanitary composition, using the calibration curve.

The results of the GC analysis are presented in Table 4 below and in FIG. 5.

TABLE 4

Results of the GC analysis of the phytosanitary composition according to the invention

| Time | Cinnamaldehyde content | | Limits min 10% | Limits max 10% |
|---|---|---|---|---|
| | Ambient temperature | 54° C. | | |
| Production | 10 | 10 | 9 | 11 |
| 0 days | 9.71 | 9.71 | 9 | 11 |
| 15 days | 9.91 | 10.07 | 9 | 11 |
| 1 month | 9.89 | 9.88 | 9 | 11 |
| 2 months | 9.74 | 9.57 | 9 | 11 |
| 3 months | 10.22 | 9.81 | 9 | 11 |

The results show that the cinnamaldehyde content of the phytosanitary composition according to the invention reduces very slightly over time, whatever the storage conditions.

EXAMPLE 7: USE OF A CONCENTRATE ACCORDING TO THE INVENTION IN THE PREPARATION OF A COSMETIC COMPOSITION—PREPARATION OF AN EMULSION

Concentrate 1 according to the invention prepared in Example 1 was used in the preparation of a cosmetic composition.

Concentrate 1 has the following characteristics:

| Components | % by weight* |
|---|---|
| Mixture of MELs | 57% |
| Radia ® 7404 | 43% |

*Percentage by weight with respect to the total weight of the concentrate.

The cosmetic composition was then prepared, by simple mixing of the concentrate according to the invention with the other 2 components described in the table below. The cosmetic composition according to the invention obtained has the following characteristics:

| Components | % by weight* |
|---|---|
| Concentrate 1 according to the invention | 7% |
| Methyl olivate (PEL-EST ® OME - Elé corporation) | 91% |
| Jojoba oil SCB (Lucas Meyer cosmetics) | 2% |

*Percentage by weight with respect to the total weight of the cosmetic composition.

An emulsion was then prepared from the cosmetic composition according to the invention obtained, as follows:

50% by weight of water, 5% by weight of the composition according to the invention, and 45% by weight of water were successively added into a flask, the percentages by weight being indicated with respect to the total weight of the water-composition mixture. The flask was then turned over in order to obtain the emulsion. If necessary, the pH and the salinity of the water will have been adjusted beforehand.

The emulsion according to the invention obtained has the following characteristics:

| Components | % by weight* |
|---|---|
| Cosmetic composition according to the invention | 5% |
| Water | 95% |

*Percentage by weight with respect to the total weight of the emulsion.

Other components can be added to this emulsion, such as other cosmetic active ingredients and/or formulation agents, the latter making it possible in particular to confer desired texture (cream, gel) and/or sensory properties on it.

EXAMPLE 8: EVALUATION OF THE STABILITY AND OF THE WETTING POWER OF EMULSIONS PREPARED FROM A CONCENTRATE ACCORDING TO THE INVENTION AND FROM COMPARATIVE CONCENTRATES

1. Materials and Methods 1.1. Material

The following products were used:

Concentrate 2 according to the invention prepared in Example 1 polyglycerol-3 caprylate/caprate (PG-3-C8/C10, C094, OLEON)

Simulsol® SL11W (SEPPIC)

methyl esters of rapeseed oil fatty acids ("EMC", Radia® 7955, OLEON NV)

2-octanol (Sigma-Aldrich)

polyethylene glycol-600 mono-oleate (Radia® 7404, OLEON)

standard water D (prepared according to the standard CIPAC MT 18.1.4)

The following equipment was used:

glass flasks, graduated test tubes, graduated pipettes a 1 mL syringe provided with a needle with a diameter of 0.63 mm a hydrophobic parafilm (Parafilm "M", NEENAH, WI 54956)

the goniometer DSA10 (KRUSS)

the "Drop shape analysis" software (KRUSS)

1.2. Methods
Preparation of the Concentrate According to the Invention
Concentrate 2 of Example 1 was used.
Preparation of the Comparative Concentrates
Comparative Concentrate 7:

40% by weight of polyglycerol-3 caprylate/caprate, 30% by weight of 2-octanol and 30% by weight of polyethylene glycol-600 mono-oleate were added into a 120 mL glass flask, the percentages by weight being indicated with respect to the total weight of the concentrate obtained, then stirred manually until homogenization of the concentrate was achieved. During stirring, the concentrate is heated at approximately 50° C. in order to facilitate the homogenization.

Comparative Concentrate 8:

40% by weight of Simulsol® SL11W, 30% by weight of 2-octanol and 30% by weight of polyethylene glycol-600 mono-oleate were added into a 120 mL glass flask, the percentages by weight being indicated with respect to the total weight of the concentrate obtained, then stirred manually until homogenization of the concentrate was achieved. During stirring, the concentrate is heated at approximately 50° C. in order to facilitate the homogenization.

standard water in test tubes, the percentages by weight being indicated with respect to the total weight of the water-composition mixture. The flasks were closed using a stopper. The flasks were then turned once.

After 30 seconds, it could be observed with the naked eye that a uniform emulsion had formed in each graduated test tube. Non-uniform (incomplete) emulsions had formed from the comparative compositions 7 and 8.

Evaluation of the Stability of Emulsions 2, 7 and 8

The stability of prepared emulsions 2, 7 and 8 was evaluated, according to step (ii) of the standard CIPAC MT 36.3.

Following observation of emulsions 2, 7 and 8 at 30 seconds, the test tubes containing these emulsions were turned over ten times then deposited in a room where they remained for 24 hours at a constant temperature of 20+/−2° C. At 30 minutes, at 1 hour, at 2 hours and at 24 hours, the volumes of free oil and/or of cream formed at the top or at the bottom of the emulsions, were measured by reading the corresponding volume on the graduated test tubes. The volumes of foam were also measured in the same way.

Results

The results are presented in Table 5 hereafter.

TABLE 5

| | Stability of emulsions 2, 7 and 8 | | | | | | | | |
|---|---|---|---|---|---|---|---|---|---|
| | Emulsion 2 | | | Emulsion 7 | | | Emulsion 8 | | |
| | Foam (mL) | Cream (mL) | Oil (mL) | Foam (mL) | Cream (mL) | Oil (mL) | Foam (mL) | Cream (mL) | Oil (mL) |
| 30 minutes | 1 | 0 | 0 | 3 | 1 | 0 | 2 | 0.5 | 0.5 |
| 1 hour | 1 | 0 | 0 | 1 | 1 | 0 | 1 | 1 | 1 |
| 2 hours | 0 | 1 | 0.2 | 1 | 1 | 0 | 1 | 1 | 1 |
| 24 hours | 0 | 0 | 1 | 0 | 2 | 0 | 0 | 2 | 2 |

Preparation of Emulsions from Concentrates 2, 7 and 8

A protocol for the preparation of emulsions from concentrate 2 according to the invention and from comparative concentrates 7 and 8 was carried out, according to step (i) of the standard CIPAC MT 36.3 ("CIPAC method 2000. Prepared by the German Formulation Panel (DAPF). Chairman: G Menschel.").

To this end, firstly, concentrates 2, 7 and 8 are brought in contact with a hydrophobic liquid according to the following protocol:

10% by weight of the different concentrates 2, 7 and 8 and 90% by weight of Radia® 7955 were added into test tubes, the percentages by weight being indicated with respect to the total weight of each composition obtained, then stirred manually until homogenization of the composition was achieved. During stirring, it is possible to heat the compositions at 40° C. in order to facilitate the homogenization. In this way compositions 2, 7 and 8 are obtained.

It is observed that comparative compositions 7 and 8 are cloudy at ambient temperature, as well as after heating at 50° C. In addition, for these two compositions, a deposit is observed at the bottom of the flask 24 hours after stirring. On the other hand, composition 2 according to the invention is homogeneous at ambient temperature, as well as after heating at 50° C. No deposit is observed at the bottom of the flask 24 hours after stirring.

These compositions 2, 7 and 8 are then brought into contact with water according to the following protocol:

1% by weight of the different compositions 2, 7 and 8 obtained were respectively added to 99% by weight of The results presented in Table 5 show that emulsion 2 according to the invention has a better stability than comparative emulsions 7 and 8. In particular, the appearance of cream in emulsion 2 according to the invention is less rapid than in comparative emulsions 7 and 8, and it can be observed that the cream is no longer present in emulsion 2 at 24 hours.

2. Evaluation of the Wetting Power of Emulsions 2, 7 and 8

Measurement of the Contact Angles

Measurements of the contact angle were carried out for each of emulsions 2, 7 and 8 and for a control solution of standard water D, using the goniometer.

To this end, a drop of each emulsion or of the control solution (3 µL) was formed using the syringe. The syringe was then placed approximately 0.5 cm above the hydrophobic parafilm. By gravity, this drop became detached from the needle and fell onto the hydrophobic parafilm. The variation in the contact angle was monitored for 10 minutes from the moment when the drop touched the parafilm, using the analysis software.

The results were then processed in order to compare the variations in contact angles for each of emulsions 2, 7 and 8, with respect to the control solution.

Results

The results of the measurements of the contact angle for each of emulsions 2, 7 and 8 and for the control solution are presented in FIG. 6.

The results show in particular that the reduction in the contact angle obtained with emulsion 2 is noticeably greater than that obtained with each of emulsions 7 and 8.

EXAMPLE 9: EVALUATION OF THE STABILITY AND OF THE THICKENING PROPERTY OF CONCENTRATES ACCORDING TO THE INVENTION AND OF COMPARATIVE CONCENTRATES

1. Obtaining the MELs

A mixture of MELS 1A was obtained by the process described in Example 1.

A step of purification of the mixture of MELs 1A was then carried out by adsorption chromatography on a silica column, with the use of a mixture of solvents having an increasing polarity gradient. A second mixture of MELs (mixture of MELs 1B) was thus obtained, which has the following characteristics:

Content of MELs: at least 98% by weight, with respect to the total weight of the mixture of MELs obtained.

In particular, the mixture of MELs 1B comprises MELs-A at a content of 52% by weight, MELs-B at a content of 12% by weight, MELs-C at a content of 35% by weight, and MELs-D at a content of 1% by weight, the percentages by weight being given with respect to the weight of the total quantity of MELs.

2. Polyethylene Glycol Fatty Acid Ester

Polyethylene glycol-600 mono-oleate ("PEG-600-oleate") marketed by OLEON NV under the trade mark RADIA® 7404 was used.

3. Preparation of Concentrates According to the Invention and of Comparative Concentrates Concentrate 9 According to the Invention 10% by weight of the mixture of MELs 1B and 90% by weight of Radia® 7404 were added into a 60 ml glass flask, the percentages by weight being indicated with respect to the total weight of the concentrate obtained, then stirred manually until homogenization of the concentrate was achieved. During stirring, it is possible to heat the concentrate at 40° C. in order to facilitate the homogenization.

Concentrate 10 According to the Invention

50% by weight of the mixture of MELs 1B and 50% by weight of Radia® 7404 were added into a 60 ml glass flask, the percentages by weight being indicated with respect to the total weight of the concentrate obtained, then stirred manually until homogenization of the concentrate was achieved. During stirring, it is possible to heat the concentrate at 40° C. in order to facilitate the homogenization.

Concentrate 11 According to the Invention

67% by weight of the mixture of MELs 1B and 33% by weight of Radia® 7404 were added into a 60 ml glass flask, the percentages by weight being indicated with respect to the total weight of the concentrate obtained, then stirred manually until homogenization of the concentrate was achieved. During stirring, it is possible to heat the concentrate at 40° C. in order to facilitate the homogenization.

Comparative Concentrate 12

Concentrate 12 only comprises Radia® 7404.

Comparative Concentrate 13

Concentrate 13 only comprises the mixture of MELs 1B.

4. Evaluation of the Stability of Concentrates 9 to 13

The stability of concentrates 9 to 13 was evaluated after storage for 1 day and for 2 months.

When a concentrate is stable, it appears in the form of a single phase. On the other hand, when a concentrate is unstable, a separation of phases between the different components of this concentrate can be observed with the naked eye.

The stability was evaluated by inspection with the naked eye.

The results are presented in Table 6 below.

TABLE 6

Stability of concentrates 9 to 13 prepared in Example 9 after storage for 1 day and for 2 months

| Concentrate | Stability after 1 day | Stability after 2 months |
| --- | --- | --- |
| Concentrate 9 | a homogeneous phase | a slightly cloudy phase |
| Concentrate 10 | a homogeneous phase | a homogeneous phase |
| Concentrate 11 | a homogeneous phase | a homogeneous phase |
| Concentrate 12 (comparative) | a homogeneous phase | Not evaluated |
| Concentrate 13 (comparative) | two phases | Not evaluated |

The results show that concentrates 9 to 11 comprising a concentrate according to the invention are stable after storage for 2 months.

5. Evaluation of the Thickening Property of Concentrates 9 to 13

10% by weight of concentrates 9 to 11 according to the invention and of comparative concentrates 12 and 13 then 90% by weight of water were respectively added into glass flasks, the percentages by weight being indicated with respect to the total weight of each concentrate/water mixture obtained. The addition of water into the flasks containing the different concentrates is carried out under manual stirring with a spatula.

The dynamic viscosity of mixtures 9 to 13 obtained was evaluated.

The viscosity is evaluated using a rheometer (TA instruments AR 2000) at 25° C., at a speed of 10 rpm.

The dynamic viscosity of water (control) is 1 mPA·s.

The results are presented in Table 7 below.

TABLE 7

Dynamic viscosities of mixtures 9 to 13 prepared in Example 9

| Mixture | Viscosity (mPA.s) |
| --- | --- |
| Mixture 9 | 1140 |
| Mixture 10 | 1270 |
| Mixture 11 | 1240 |
| Mixture 12 (comparative) | 33 |
| Mixture 13 (comparative) | Not applicable |

The results show that mixtures 9 to 11 comprising a concentrate according to the invention and water have a dynamic viscosity clearly greater than that of pure water. On the other hand, mixtures 12 and 13 comprising the comparative concentrates have a viscosity close to that of water.

A concentrate according to the invention has a good thickening property, and can therefore be used as thickening agent.

EXAMPLE 10: EVALUATION OF THE EMULSIFIABILITY OF COMPARATIVE COMPOSITIONS COMPRISING A NON-IONIC SURFACTANT HAVING AN HLB VALUE OF LESS THAN 12

1. Materials and Methods 1.1 Material

The products that were used in this example are the following:

the mixture of MELs 1A prepared in Example 1
methyl esters of rapeseed oil fatty acids (Radia® 7955 OLEON NV)
polyethylene glycol-600 di-oleate (Radia® 7444, OLEON NV, HLB: 10)
polyethylene glycol-200 mono-oleate (Radia® 7402, HLB: 7)
2-octanol (Sigma-Aldrich)
standard water D (prepared according to the standard CIPAC MT 18.1.4)
The following equipment was also used in this example:
60 mL glass flasks
100 mL graduated test tubes
5 mL graduated pipettes
1.2. Methods
Preparation of Comparative Concentrates
Comparative Concentrate 14
40% by weight of the mixture of MELs, 30% by weight of 2-octanol and 30% by weight of Radia® 7444 were added into a 60 ml glass flask, the percentages by weight being indicated with respect to the total weight of the concentrate obtained, then stirred manually until homogenization of the concentrate was achieved. During stirring, it is possible to heat at 40° C. in order to facilitate the homogenization.
Comparative Concentrate 15
40% by weight of the mixture of MELs, 30% by weight of 2-octanol and 30% by weight of Radia® 7402 were added into a 60 ml glass flask, the percentages by weight being indicated with respect to the total weight of the concentrate obtained, then stirred manually until homogenization of the concentrate was achieved. During stirring, it is possible to heat at 40° C. in order to facilitate the homogenization.

Evaluation of the Surfactant Properties of Concentrates 14 and 15

A protocol for the preparation of emulsions from concentrates 14 and 15 was carried out, according to step (i) of the standard CIPAC MT 36.3 ("*CIPAC method* 2000. *Prepared by the German Formulation Panel (DAPF). Chairman: G Menschel.*").

Firstly, concentrates 14 and 15 are brought into contact with a hydrophobic liquid according to the following protocol:
10% by weight of concentrate 14 or 15 and 90% by weight of Radia® 7955 were added into a flask, the percentages by weight being indicated with respect to the total weight of the composition obtained, then stirred manually until homogenization of the composition was achieved. During stirring, it is possible to heat the composition at 40° C. in order to facilitate the homogenization,
In this way comparative compositions 14 and 15 are obtained.

These compositions 14 and 15 are then brought into contact with water according to the following protocol:
1% by weight of the different compositions 14 and 15 were respectively added to 99% by weight of standard water in graduated test tubes.
The graduated test tubes were closed using a stopper. The graduated test tubes were then turned once.
After 30 seconds, it could be observed with the naked eye that non-uniform (incomplete) emulsions had formed in the test tubes: droplets were present in each test tube.
These tests can be compared with the test of Example 2 carried out with concentrate 2 according to the invention, comprising 40% by weight of the mixture of MELS, 30% by weight of 2-octanol and 30% by weight of polyethylene glycol-600 mono-oleate having an HLB=13.2.

The invention claimed is:

1. A concentrate comprising:
at least one mannosylerythritol lipid (MEL), and
at least one polyethylene glycol fatty acid ester having an HLB value greater than or equal to 12,
in which the MEL:polyethylene glycol fatty acid ester ratio is comprised between 0.1 and 2.

2. The concentrate according to claim 1, further comprising at least one alcohol having a number of carbon atoms comprised between 1 and 16.

3. The concentrate according to claim 1, wherein the polyethylene glycol fatty acid ester has an HLB value comprised between 12 and 20.

4. The concentrate according to claim 1, wherein the total quantity of MEL(s) is between 1 and 90% by weight, with respect to the total weight of the concentrate.

5. The concentrate according to claim 1, wherein the total quantity of polyethylene glycol fatty acid ester(s) is between 1 and 90% by weight, with respect to the total weight of the concentrate.

6. The concentrate according to claim 1, comprising at least two MELs selected from the group consisting of MEL-A, MEL-B, MEL-C and MEL-D.

7. The concentrate according to claim 1, further comprising at least one free fatty acid and/or at least one triglyceride.

8. An emulsion comprising a concentrate according to claim 1, a hydrophobic liquid, and water.

9. A phytosanitary composition comprising a concentrate according to claim 1 and a pesticide active ingredient.

10. A cosmetic composition comprising a concentrate according to claim 1 and a cosmetic active ingredient.

11. A phytosanitary composition comprising an emulsion according to claim 8, and a pesticide active ingredient.

12. A cosmetic composition comprising an emulsion according to claim 8, and a cosmetic active ingredient.

* * * * *